(12) United States Patent
Posner

(10) Patent No.: US 6,994,730 B2
(45) Date of Patent: Feb. 7, 2006

(54) MENISCAL AND TIBIAL IMPLANTS

(75) Inventor: Elliot Posner, New York, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 113 days.

(21) Appl. No.: 10/356,263

(22) Filed: Jan. 31, 2003

(65) Prior Publication Data

US 2004/0153163 A1 Aug. 5, 2004

(51) Int. Cl.
A61F 2/38 (2006.01)
(52) U.S. Cl. .................................... 623/20.32
(58) Field of Classification Search ............. 623/20.32, 623/20.34, 20.36, 20.35, 20.21, 20.29, 20.14, 623/20.33; 606/79; 128/898
See application file for complete search history.

(56) References Cited

U.S. PATENT DOCUMENTS

| 3,715,763 | A | * | 2/1973 | Link ........................... 623/20.3 |
| 4,055,862 | A | * | 11/1977 | Farling ..................... 623/18.11 |
| 4,344,193 | A | | 8/1982 | Kenny |
| 4,502,161 | A | * | 3/1985 | Wall ......................... 623/14.12 |
| 4,728,332 | A | * | 3/1988 | Albrektsson ............. 623/20.29 |
| 4,919,667 | A | | 4/1990 | Richmond |
| 5,007,934 | A | | 4/1991 | Stone |
| 5,067,964 | A | | 11/1991 | Richmond et al. |
| 5,171,322 | A | | 12/1992 | Kenny |
| 5,308,412 | A | | 5/1994 | Shetty et al. |
| 5,683,469 | A | * | 11/1997 | Johnson et al. .......... 623/20.32 |
| 5,735,903 | A | | 4/1998 | Li et al. |
| 5,879,387 | A | | 3/1999 | Jones et al. |
| 6,042,610 | A | | 3/2000 | Li et al. |
| 6,059,831 | A | * | 5/2000 | Braslow et al. ............. 128/898 |
| 6,206,927 | B1 | | 3/2001 | Fell et al. |
| 6,503,280 | B2 | * | 1/2003 | Repicci ................... 623/20.14 |
| 2001/0023373 | A1 | | 9/2001 | Plouhar |
| 2002/0022884 | A1 | | 2/2002 | Mansmann |
| 2002/0022889 | A1 | * | 2/2002 | Chibrac et al. .......... 623/18.11 |
| 2002/0147498 | A1 | | 10/2002 | Tallarida et al. |
| 2002/0173855 | A1 | | 11/2002 | Mansmann |

FOREIGN PATENT DOCUMENTS

| EP | 1 169 980 A2 | 1/2002 |
| EP | 1 277 450 | 1/2003 |
| WO | WO-01/70142 | 9/2001 |
| WO | WO-03/007787 A2 | 1/2003 |

* cited by examiner

Primary Examiner—Pedro Philogene
(74) Attorney, Agent, or Firm—Lerner, David, Littenberg, Krumholz & Mentlik, LLP

(57) ABSTRACT

Instrumentation and a method for resurfacing a joint capsule having cartilage and meniscal surfaces such as a knee joint includes resecting a central portion of the joint cartilage on one joint member such as the tibia while leaving a meniscal rim attached to the peripheral joint capsule. A cavity is then formed in the bone underlying the central portion of the joint surface such as the lateral tibial surface. A resurfacing implant is then coupled, by cementing for example, to the cavity. A soft prosthetic meniscal implant is then coupled to the remaining meniscal ring such as by suturing.

24 Claims, 14 Drawing Sheets

MENISCAL AND TIBIAL IMPLANTS

BACKGROUND OF THE INVENTION

This invention relates to surgical implants that are designed to replace meniscal tissue and cartilage in a mammalian joint, such as a knee joint and methods to implant the same. While a knee is the primary joint of concern, the invention applies to other body joints as the hip, shoulder, elbow, temporomandibular, sternoclavicular, zygapophyseal, and wrist.

Compared to the hip the knee has a much greater dependence on passive soft tissues (menisci, ligaments, and the joint capsule) for stability and function. Although the mechanics of the two joints are different, known hip and knee implants are very similar in design, both consisting of a semi-rigid on rigid (polyethylene on CoCr) bearing surface. In many prosthetic knee implants, function and mobility are impaired because rigid structures are used to replace the natural soft tissues.

Normal anatomical knees have two pliable, mobile menisci that function to absorb shock, distribute stress, increase joint congruity, increase contact area, guide arthrokinematics, help lubrication by maintaining a fluid-film bearing surface, and provide proprioceptive input, i.e., nerve impulse via its attachment to the joint capsule. Even under physiologic loading a natural knee with natural menisci will primarily distribute stresses through a fluid film, only 10% of a load is transmitted via a solid on solid contact. Due to the fluid film bearing surface contact wear is greatly reduced. In simple terms the menisci function to reduce joint stresses, decrease wear, and help guide normal kinematics. Without menisci, peak contact stresses in the knee increase by 235% or more and degenerative changes start to progress rapidly. At 0°, 30°, and 60° of flexion, natural knees with intact menisci have approximately 6 to 8 times the contact area of typical prosthetic knee implants many of which have a similar geometry to that of a natural knee without menisci.

Typical existing knee replacements lack the functional features normally provided by the menisci and the common polyethylene on metal such as cobalt chrome (CoCr) bearing interface lacks the wear-reducing fluid film bearing surface. By adding a well-designed meniscal substitute, many shortcomings of existing knee replacements can be addressed. In theory, prosthetic menisci could have the same impact on a prosthetic knee as natural menisci do for natural knees.

The prosthetic knee meniscus of the present invention has at least one and preferably two compliant prosthetic menisci (medial and lateral in the knee) that are attached to the joint capsule and meniscal horns in a similar fashion to the way a natural meniscus is attached to a natural knee. Like a natural meniscus, the meniscal knee implant of the present invention will be able to pivot and glide on a prosthetic tibial plateau. Arthrokinematic constraint comes from the meniscal attachments and will gently guide movements, providing a highly mobile but stable joint. Also through its attachments, the Anatomical Meniscal-Bearing Knee will provide proprioceptive input, giving the central nervous system feedback for refined motor control.

A preferred material for the meniscal implant of the present invention is polyurethane. Polyurethane can be made flexible so it can conform to the femoral and tibial components, thus giving the knee a large contact area throughout the entire range of motion. Such a polyurethane is described in U.S. Pat. No. 5,879,387. Alternatively, a hydrogel such as a poly(vinyl) alcohol can be used as a prosthetic meniscal implant. Such a hydrogel can be cross-linked to increase its strength and wear properties. Like cartilage, it imbibes aqueous fluids and generates a fluid-film bearing surface.

The flexible, pliable, gel-like nature of a synthetic hydrogel (when saturated with water) arises mainly from crosslinking attachments between non-parallel fibers in the gel. Depending on the specific polymeric structure that has been chosen, these crosslinking attachments between the long "backbone" chains in a polymer can be formed by covalent bonding, by hydrogen bonding or similar ionic attraction, or by entangling chains that have relatively long and/or "grabby" side-chains.

Regardless of which type of bonding or entangling method is used to bind the backbone chains together to form a hydrogel, the "coupling" points between molecular chains can usually be flexed, rotated, and stretched.

In addition, it should be recognized that the back-bone chains in hydrogel polymers are not straight; instead, because of various aspects of interatomic bonds, they are somewhat kinked, and can be stretched, in an elastic and springy manner, without breaking the bonds.

In a typical hydrogel, the fibers usually take up less than about 10% of the volume; indeed, many hydrogels contain less than 2% fiber volume, while interstitial spaces (i.e., the unoccupied spaces nestled among the three-dimensional network of fibers, which become filled with water when the gel is hydrated) usually make up at least 90 to 95% of the total volume. Accordingly, since the "coupling" point between any two polymeric backbone chains can be rotated and flexed, and since any polymeric backbone molecule can be stretched without breaking it, a supple and resilient gel-like mechanical structure results when a synthetic hydrogel polymer is hydrated.

Various methods are known for creating conventional polymeric hydrogels. A number of such methods involve mixing together and reacting precursor materials (monomers, etc.) while they are suspended in water or other solvent. This step (i.e., reacting two or more monomers while they are suspended in a solvent) gives a desired density and three-dimensional structure to the resulting polymerized strands or fibers. The resulting material is then frozen, to preserve the desired three-dimensional structure of the fibers. The ice (or other frozen solvent) is then vaporized and removed, without going through a liquid stage, by a sublimizing process (also called lyophilizing), using high vacuum and low temperature. After the solvent has been removed, any final steps (such as a final crosslinking reaction and/or rinsing or washing steps, to remove any unreacted monomers, crosslinking agents, quenching agents, etc.) are carried out. The polymer is then gradually warmed up to room temperature, and it is subsequently saturated with water, to form a completed hydrogel.

In the past, effort mainly has been placed on the development of meniscal replacement. In the attempt to repair or replace torn menisci, allographs, xenographs, and autographs have been implanted for over 20 years. Current focus has been on the development of collagen-matrix meniscal implants. However, these implants do not reproduce the mechanical properties of a normal meniscus.

As used herein, all references to "implants" or "implantation" (and all terms such as surgery, surgical, operation, etc.) refer to surgical or arthroscopic implantation of a reinforced hydrogel device, as disclosed herein, into a mammalian body or limb, such as in a human patient. Arthroscopic methods are regarded herein as a subset of surgical methods, and any reference to surgery, surgical, etc., includes arthroscopic methods and devices. The term "minimally invasive" is also used occasionally herein, even though it is imprecise; one should assume that any surgical operation will be done in a manner that is minimally invasive, in view of the needs of the patient and the goals of the surgeon.

Meniscal Tissues in Knees—Each knee joint of a human contains a "medial" meniscus, and a "lateral" meniscus. The lateral meniscus is located on the outer side of the leg, directly above the location where the upper end of the fibula bone is coupled to the tibia ("shinbone"). The medial meniscus is located on the inner side of the leg.

Each meniscus (also referred to, especially in older texts, as a "semilunar fibrocartilage") has a wedged shape, somewhat comparable to a segment from an orange or other citric fruit, but with a substantially larger curvature and "arc." The thickest region is around the periphery (which can also be called the circumference, the rim, and similar terms). When implanted into a knee, this peripheral rim normally will be anchored to the surrounding wall of a fibrous "capsule" which encloses the knee joint and holds in the synovial fluid, which lubricates the cartilage surfaces in the knee. The two ends of each semi-circular wedge are coupled, via thickened collagen structures called horns to the "spine" protrusions in the center of the tibial plateau.

The inner edge of a meniscus is the thinnest portion of the wedge; this edge can also be called the apex, the margin, and similar terms. It is not anchored; instead, as the person walks or runs, each meniscus in a knee is somewhat free to move, as it is squeezed between the tibial plateau (beneath it) and a femoral runner or condyle (above it). The bottom surface of each meniscus is relatively flat, so it can ride in a relatively stable manner on top of the tibial plateau. The top surface is concave, so it can provide better, more closely conforming support to the rounded edge of the femoral runner. Because of its shape, location, and ability to flex and move somewhat as it is pushed, each meniscus helps support and stabilize the outer edge of a femoral runner, as the femoral runner presses, slides, and "articulates" against the portion of the tibial plateau beneath it.

However, because all four of the menisci inside a person's knees are in high-stress locations, and are subjected to frequently-repeated combinations of compression and tension (and sometimes abrasion as well, especially in people suffering from arthritis or other forms of cartilage damage), meniscal damage often occurs in the knees of humans, and occasionally other large animals.

It should be noted that, in humans, meniscal-type tissues also exist in temporomandibular, sternoclavicular, zygapophyseal, and wrist joints.

Various efforts have been made, using prior technology, to repair or replace damaged meniscal tissue. However, because of the complex structures and anchoring involved, and because of the need to create and sustain extremely smooth and constantly wet surfaces on the inner portions of each meniscal wedge, prior methods of replacing or repairing damaged meniscal are not entirely adequate.

Many meniscal implants for the knee address the need for attachment to the surrounding soft tissue but they do not address the need to resurface the femoral and/or the tibial articulating surfaces. An example of this type of implant is described by Kenny U.S. Pat. No. 4,344,193 and Stone U.S. Pat. No. 5,007,934.

A free-floating cobalt chrome meniscal replacement has been designed to cover the tibial bearing surface. Because this implant is rigid and because it is disconnected from the soft tissues it lacks the ability to shock absorb and/or provide proprioceptive input. In fact, because it is approximately 10–20 times more rigid than bone it may actually cause concentrated loading, increased contacts stresses, and therefore accelerate degenerative joint changes.

Various unicondylar knee implants for joint replacement contain a meniscus-like component. The tibial-bearing component of the known Oxford Knee (British Patent Application No. 49794/74) contains a free-floating piece of polyethylene that can glide or spin on a polished, flat, tibial CoCr surface in the transverse plane. The tibial-bearing component in turn articulates with the CoCr femoral implant. Because the polyethylene meniscus is semi-rigid it has a limited capacity to absorb shock or conform to the femoral component. Because of its materials, the Oxford knee also lacks a wear-reducing fluid film bearing surface.

SUMMARY OF THE INVENTION

The anatomical meniscal-bearing knee implant of the present invention has one or more compliant prosthetic menisci that are attached to the joint capsule and meniscal horns in a similar fashion to the way a natural meniscus is attached to a natural knee. Like a natural meniscus, the meniscal implant will be able to pivot and glide on the prosthetic tibial plateau. Arthrokinematic constraint will come from the meniscal implant's attachments, which will gently guide movements, providing a highly mobile but stable joint. Also through its attachments, the Anatomical Meniscal-Bearing Knee will provide proprioceptive input, giving the central nervous system feedback for refined motor control. Like a natural knee with intact menisci, the outer border of the menisci implants will be mechanically linked to the tibial plateau via the coronary ligament, such as for example by the implant being attached such as by its being sutured directly to the joint capsule/coronary ligament or indirectly by attaching it to the remaining meniscal rim which is in turn attached to the coronary ligament. Tendon slips from the quadriceps, attached to both medial and lateral meniscus, will pull the meniscal replacements forward during active extension and likewise, the semimembranosus (medial meniscus) and/or popliteus tendons (lateral meniscus) will pull the meniscal replacements posteriorly during active flexion.

The proposed anatomical meniscal-bearing arthroplasty has one or multiple prosthetic menisci that are attached to either the diarthrodial joint capsule and/or the remnant of the natural menisci. The knee will be used to describe the preferred embodiment of this concept. However, the proposed meniscal bearing can be used to repair cartilage in other body joints.

The prosthetic is preferably implanted in the knee via a minimally invasive procedure, leaving the quadriceps muscle group intact. A small arthrotomy will be performed, allowing the access to the knee joint. Then the central portion of the meniscus will be resected, leaving the horns, a peripheral meniscal rim, and the coronary ligament intact. One or more well-defined cavities will then be formed in the articular surfaces of the tibia and/or femur. One or more resurfacing implants would then either be press-fit, cemented or sutured into the prepared pocket. The meniscal prosthetic is then sewed into the meniscal rim.

The non-meniscal articular resurfacing portion of the implants which contact the meniscus consists of cobalt chrome alloys, stainless steel, ceramics, polyethylene, and/or polyurethane and will closely approximate the normal articular geometry.

The bulk of the meniscal prosthetic implant will preferably consist of a compliant polyvinyl alcohol polymer and/or polyurethane. A meshed fabric may be molded into the peripheral rim of the prosthetic body, allowing biological glues and/or sutures to connect the implant to the surrounding soft tissue. If the entire original meniscus needs to be removed, a flexible tube can be placed in the space bordered by the tibial plateau, coronary ligament, and anatomical meniscus in order to measure the natural soft tissue laxity. Different diameters of tubing represent different amounts of laxity/mobility in the natural meniscus/coronary ligament construct. This tubing can then be reused as a spacer to balance the soft tissue connections, simulating the restraint of the natural meniscus.

One preferred material for the meniscal implant is polyurethane. Polyurethane can be made flexible so it can conform to the femoral and tibial components, thus giving the knee a large contact area throughout the entire range of motion. Likewise, a polyvinyl alcohol polymer which imbibes aqueous fluids can be used. Like cartilage, it imbibes aqueous fluids and generates a fluid-film-bearing surface.

The shape of the meniscal implants will closely conform to the tibial plateaus and femoral condyles, generating large areas of contact. They can either be congruent or, to distribute stresses more evenly they can be slightly incongruent as described by Goodfellow et al., The Design of Synovial Joints, Scientific Foundations of Orthopaedics and Traumatology, pp. 78–88. The meniscal portions of the implant will be flexible so they can conform to the tibial and femoral bearing surfaces throughout the entire range of motion.

The anatomical meniscal-bearing concept could also be used in a unicondylar knee replacement. Because the meniscal portion of the implant is able to spin and glide on the tibial plateau, and because the meniscal replacement is flexible, the implant will be less sensitive to malalignement. With existing unicondylar knee replacements if the implant is malaligned the entire joint will likely experience abnormal stresses.

Another possible use for this implant would be in the meniscal replacement surgery. The meniscal portion of the implant can be used by itself, being sewed to the joint capsule and meniscal horns of the knee. Also, variation in the meniscal implant can be made for replacement of menisci from other joints, i.e., sternoclavicular, temperomandibular, and zygapophyseal.

The invention also relates to a surgical procedure which is minimally invasive when compared to standard techniques currently used for resurfacing the knee joint or other body joints. In this method, the incision length is limited between 2 and 2½ times the patellar width. During forming the incision, the surgeon should avoid turning the patella (everting) over from its natural position. Steps should also be taken to leave the quadriceps muscle in its natural position by making sure it is not severed or twisted. Attachments to the peripheral tibial plateau, horns and surrounding ligaments and musculature is maintained through the meniscal rim. For example, the anterior cruciate ligament, if attached to the meniscal rim, should be maintained. Likewise, the transverse ligament should be left attached to the meniscal horns. The inner portion of the meniscus is then removed. Preferably, the incision/resection is made within or at the border of the zone of the meniscus known as the red or vascularized region. Tibial sizing guides are used to measure the size of the meniscal resection (length of resection arc and thickness at the red-zone border).

If femoral resurfacing is needed, the femoral resection may be done using a femoral alignment guide which has a rod extending externally of the incision, which rod points to the femoral head. The rod indicates implant flexion and implant rotation within the frontal plane. Once properly aligned, a femoral sizing template is used to measure and guide a posterior femoral cut. Obviously, there will be several different size templates corresponding to the several femoral implant sizes. The template may include a saw blade slot for preparing the posterior surface of the femur.

A tibial-sizing tray is utilized to prepare the tibial bone cuts within the inner portion of the meniscus. Preferably, the meniscus will be removed in an oval or "D"-shape with the oval aligned with the two anatomic meniscal horns. Obviously, again, there are various size templates corresponding to different size tibias. Once aligned, the tray template is pinned in position and a burr or end mill is used to mill a pocket into the tibial plateau. A second template or deeper layer of the first template-shaped like an "I" beam (if a second template is used, it is placed over the pins after the initial template is removed) and a deeper recess is formed within the initial recess or cavity. In other words, the "I"-shaped pocket is deeper than the original "D"-shaped or oval pocket to accommodate an "I"-shaped keel on the implant. Preferably as the "D"-shaped pockets grow in size, the "I"-shaped keel receiving recess also increases, however, it may remain the same size if desired. The "D"-shaped pocket formed should encompass the entire tibial plateau within the rim with the "I"-shaped recess in the center.

On the femoral side, a femoral burr template is pinned in position and a recess of general uniform depth is formed, as by milling with a burr, along the condyle of the distal femur. A femoral implant, preferably made of a cobalt chrome alloy such as Vitallium® alloy or a ceramic material is implanted in the recess formed on the femoral condyle. Preferably, this implant has a thickness corresponding to the depth of the recess formed so that the outer surface of the implant is located at the correct anatomical position.

A tibial resurfacing implant is provided and has a "D"-shaped corresponding the various size templates provided. For each implant profile, several implant thicknesses are provided. The thickness is chosen such that the implant will be aligned in the varus/valgus direction. Once the implant thickness is determined, the actual implant will either be press fit or cemented into place. The tibial plateau implant has a contact surface preferably made of polyethylene and will have a porous titanium surface against the bone. The bone contacting porous surface attached to the polyethylene preferably is made of titanium or cobalt chrome or any other biocompatible porous material. Alternatively, the tibial implant can be made of polyurethane, cobalt chrome, ceramics, or a polyvinyl alcohol hydrogel. Alternatively, the implant may be in the shape of a circular disc with a periphery located immediately inside the remaining rim of the tibia.

Once the tibial plateau is resurfaced, a meniscal implant is attached to the remaining meniscal rim such by suturing. A sizing template is used to determine the required implant size in all three anatomical planes. The meniscus, which is attached to the remaining rim of the tibial plateau is preferably made of a polyvinyl alcohol hydrogel or a polyurethane but can be made of any biocompatible soft, compliant material that is able to withstand the functional loading and tribiological conditions. The implant is sutured into the remaining meniscal rim. The sutures can be made part of the implant such as by molding. See, for example, the implant of Kenny U.S. Pat. No. 4,344,193. The sutures may be made integral with a mesh that is also molded into the implant. The mesh can abut the meniscal rim and allow for the potential of soft tissue ingrowth. Bioactive factors such as tissue cultures, resorbables, bone morphogenic proteins can be added to the mesh to encourage the tissue ingrowth. See Stone U.S. Pat. No. 5,007,934.

DETAILED DESCRIPTION

Figure 1:
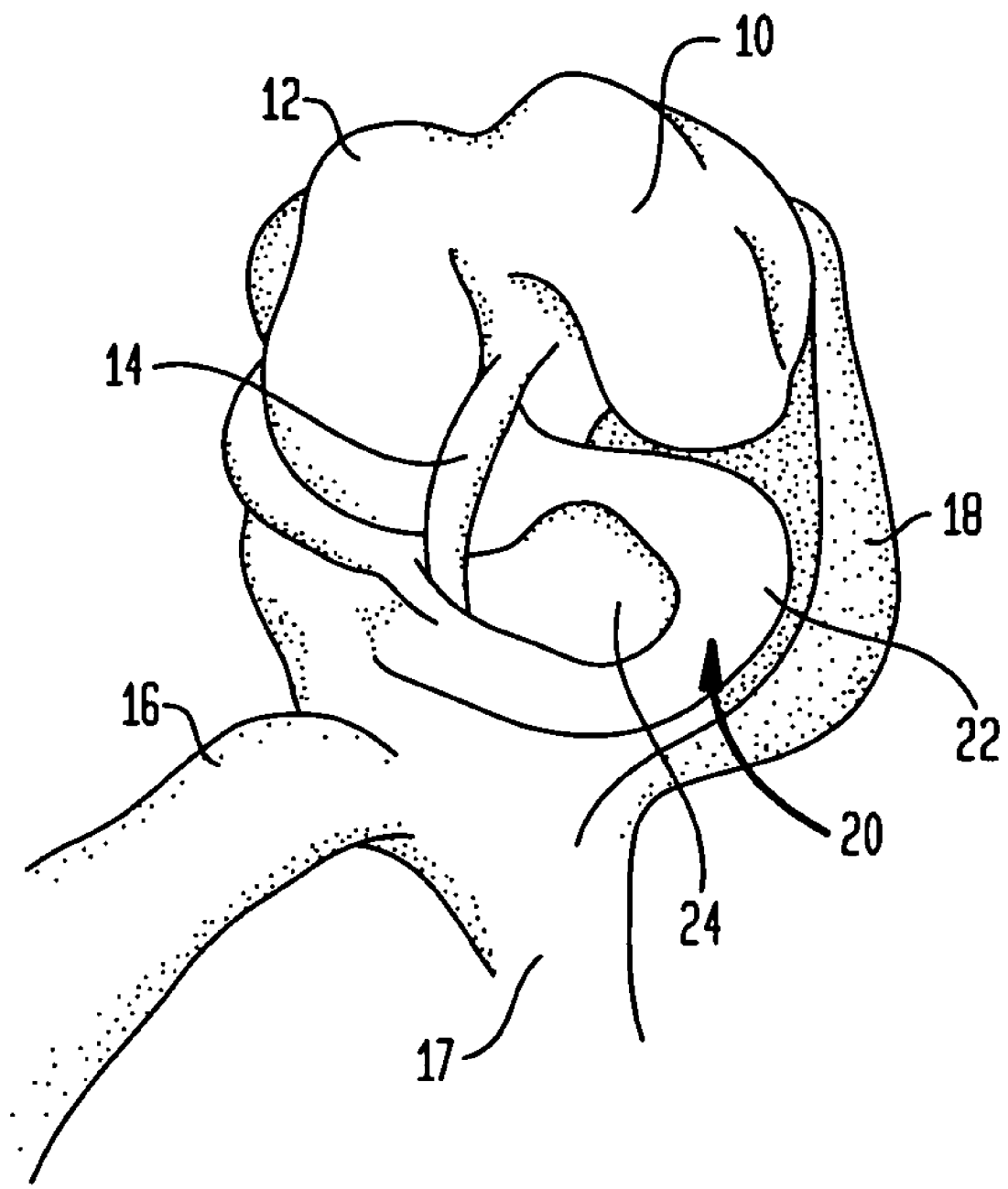
FIG. 1 is an isometric view of a knee joint capsule showing the exposed tibial meniscal portions.

Referring to FIG. 1 there is shown, for purposes of reference, an open knee joint capsule including a lateral femoral condylar surface 10 and a medial femoral condylar surface 12. The anterior cruciate ligament 14 is shown running through the joint. The quadriceps 16 is shown coupled to the tibia 17 and the lateral collateral ligament 18 is shown connecting the tibia and the femur. The lateral meniscus 20 which includes a rim area 22 is located above the tibial plateau 24.

Figure 2:
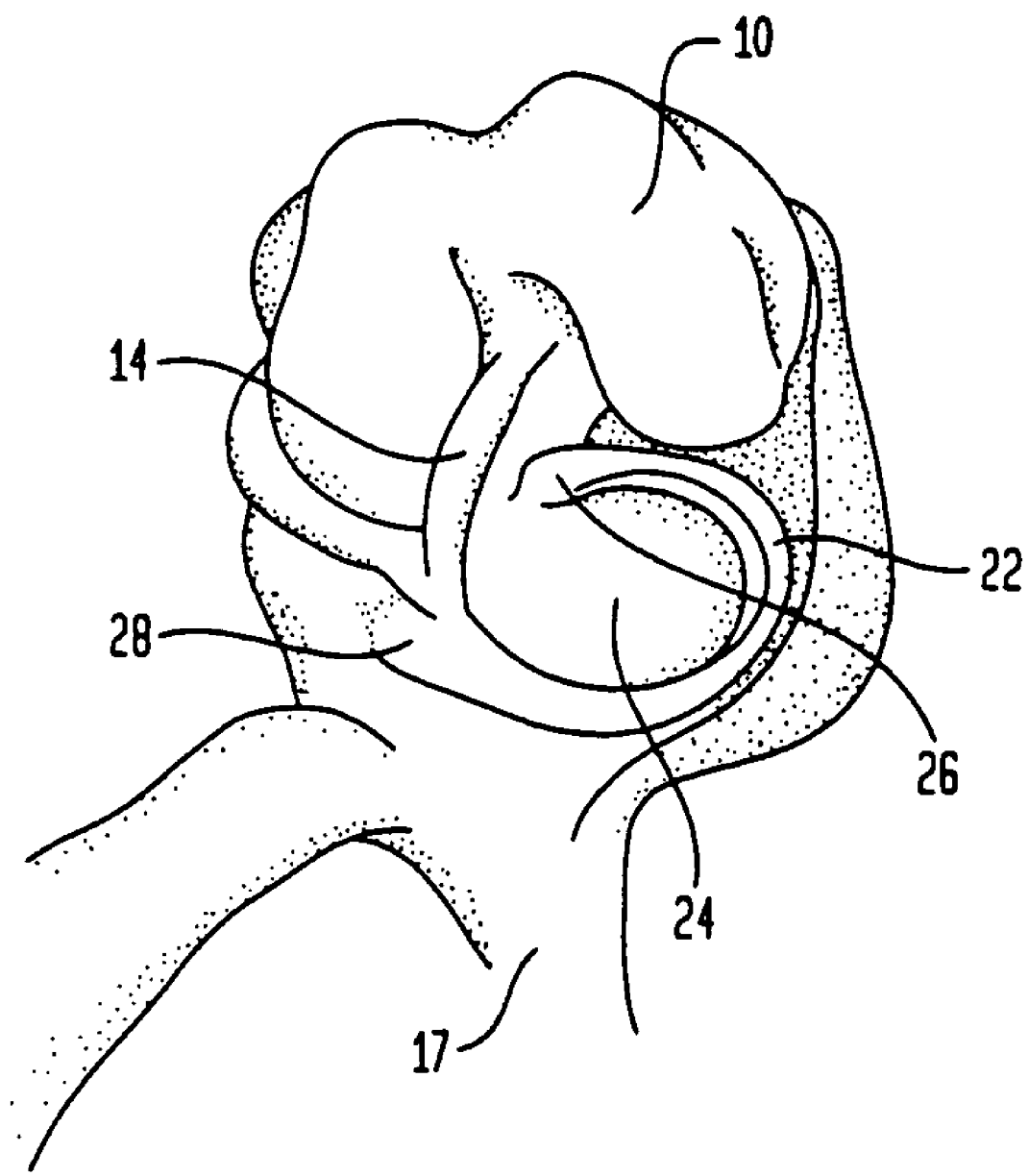
FIG. 2 shows the capsule of FIG. 1 after removal of the central portion of the lateral meniscus but leaving a meniscal rim.

Referring to FIG. 2, there is shown the joint capsule of FIG. 1 with the inner portion of the meniscus 20 removed leaving meniscal rim 22. In the preferred method, which will be discussed below, the incision/resection of the meniscus 20 is made within or at the border of what is known as the red zone of the meniscus, i.e., the vascularized region of the meniscus. The resection of the inner part of meniscus 20 leaves meniscal horns 26, 28 in place. Since the meniscal rim 22 remains, all the attachment points to the peripheral tibial plateau 24 are left and the surrounding ligaments and musculature is maintained through the meniscal rim.

Figure 3:
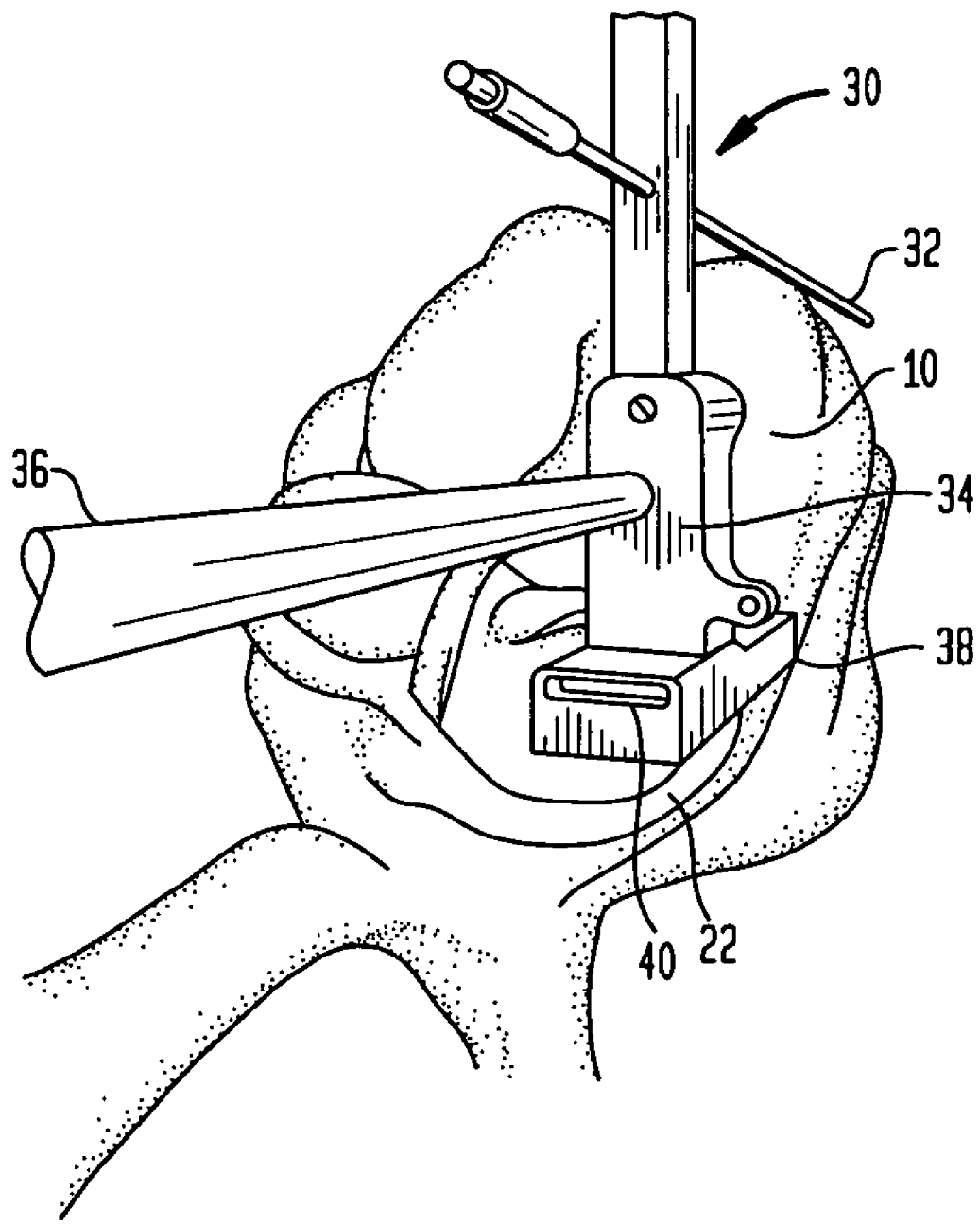
FIG. 3 shows the location of a femoral sizing template and alignment guide mounted within the joint capsule.

Referring to FIG. 3, a femoral alignment guide 30 includes an alignment rod 32 which extends outwardly of the knee capsule and can be aligned with the femoral head and laid parallel to the femoral shaft in the frontal plane for referencing the location of the femoral sizing template. Specifically, implant flexion and implant rotation with regard to the frontal and sagittal planes can be set. A femoral sizing template 34 is thus aligned with alignment guide 30 on the lateral condyle 10 of the femur. In the preferred embodiment, femoral sizing template 34 includes a handle 36 and a posterior saw guide 38. The posterior saw guide 38 is used to make the posterior femoral cut via a slotted saw guide 40.

Figure 4:
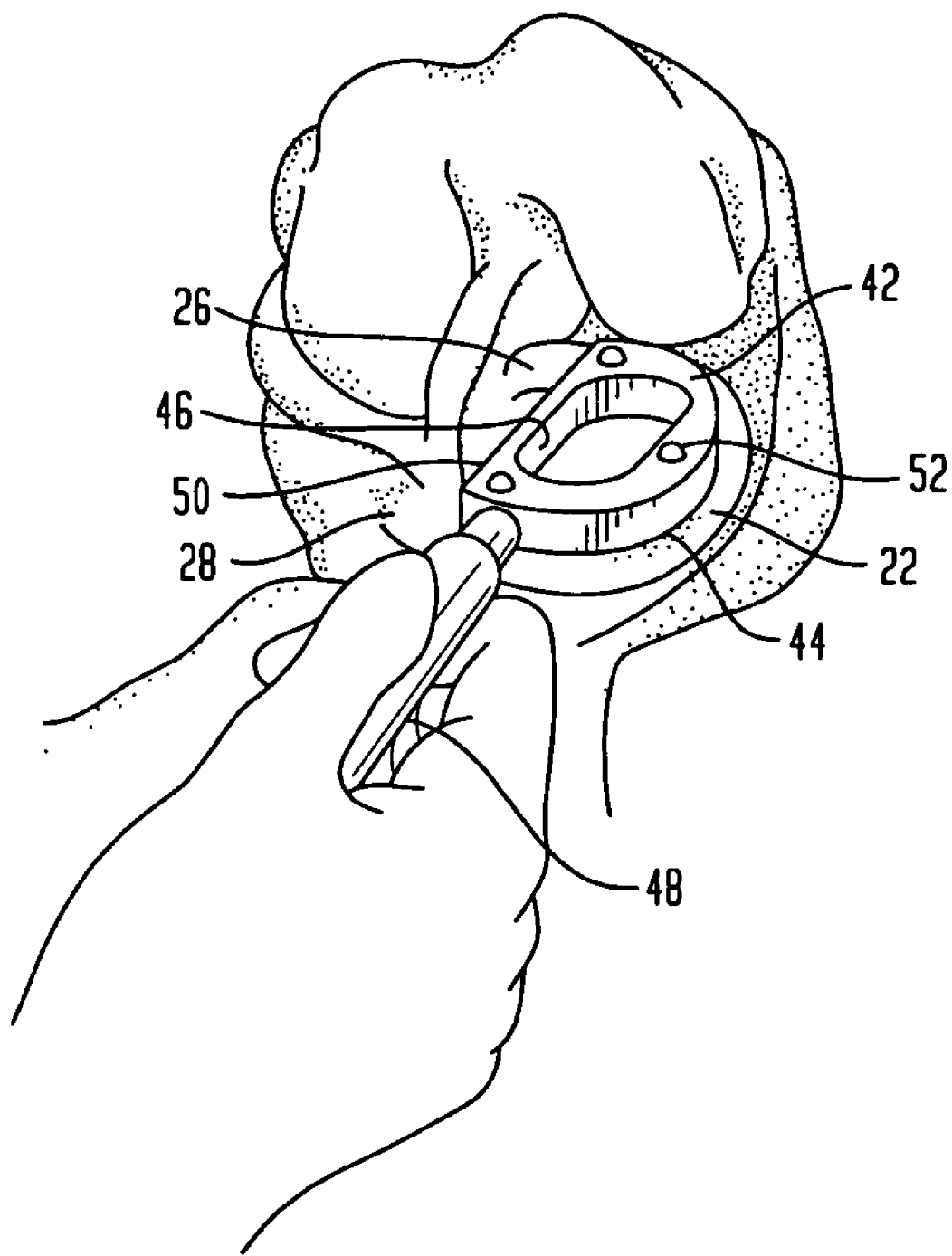
FIG. 4 shows a tibial tray sizing template located within the remaining meniscal rim on the tibial plateau.

With regard to FIG. 4, there is shown a tibial sizing template 42. In the preferred embodiment, template 42 has a "D"-shaped outer surface 44 and a generally oval inner surface 46. In the preferred embodiment, template 42 includes a handle 48 so that a straight side 50 of the "D"-shaped template 42 may be aligned with the meniscal horns 26, 28. Preferably, a series of templates 42 of varying sizes are provided in a kit, each corresponding to a population of different size tibial plateaus. It is contemplated that a series of 5 to 7 templates 42 would be provided in a kit to be used during the surgical procedure. This is also true for template 34 in which a variety of sizes may be provided to accommodate different size femurs. In the preferred embodiment, template 42 includes a series of through bores 52.

Figure 5:
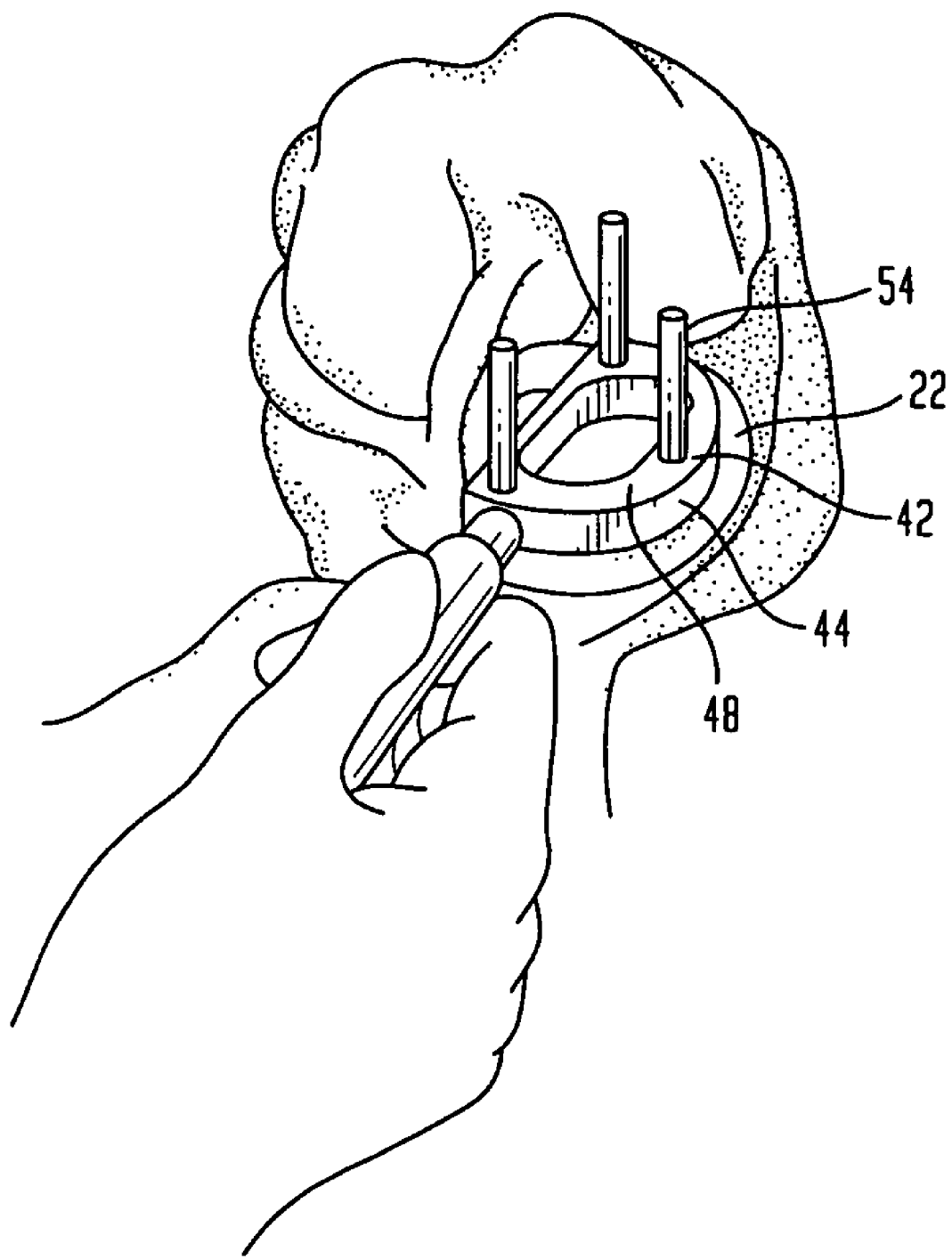
FIG. 5 shows the template of FIG. 4 pinned in a position aligned with the meniscal horns.
Figure 6:
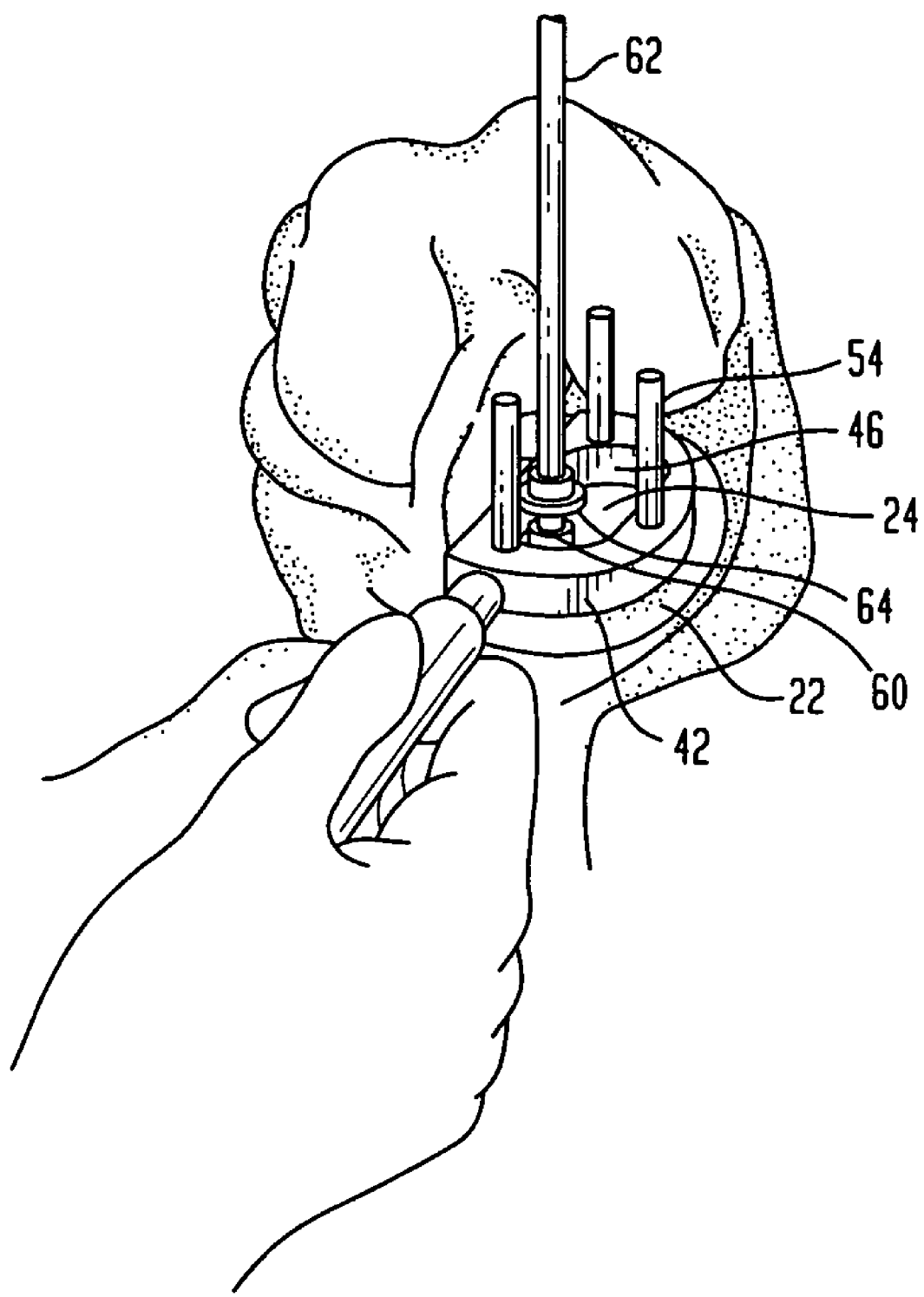
FIG. 6 shows a burr used to mill a pocket in the tibial plateau conforming to the tibial sizing template.

Referring to FIG. 5, there is shown the template 42 of FIG. 4 pinned in position utilizing three pins 54 which are sunk into the bone of the tibial plateau through holes 52 of "D"-shaped template 42. Pins 54 locate template 42 on the tibial plateau in a location which, in the preferred embodiment, places a surface 44 of template 42 in close proximity of the remaining rim portion 22 of the natural meniscus. As can be seen in FIG. 6, there is shown a burr or end mill 60 which is used to form a recess surface in tibial plateau 24 having the shape of inner surface 46 of template 42. Burr 60 is driven by any convenient means via a drive shaft 62. In the preferred embodiment, burr 60 includes a stop plate 64 which contacts an upper surface 48 of template 42. Stop plate 64 is set at a predetermined distance from the lower most cutting face of mill or burr 64 so that a depth of resection into the surface of tibial plateau 24 is set. In the preferred embodiment, this is at least 0.2 and preferably 0.24 inches.

Figure 7:
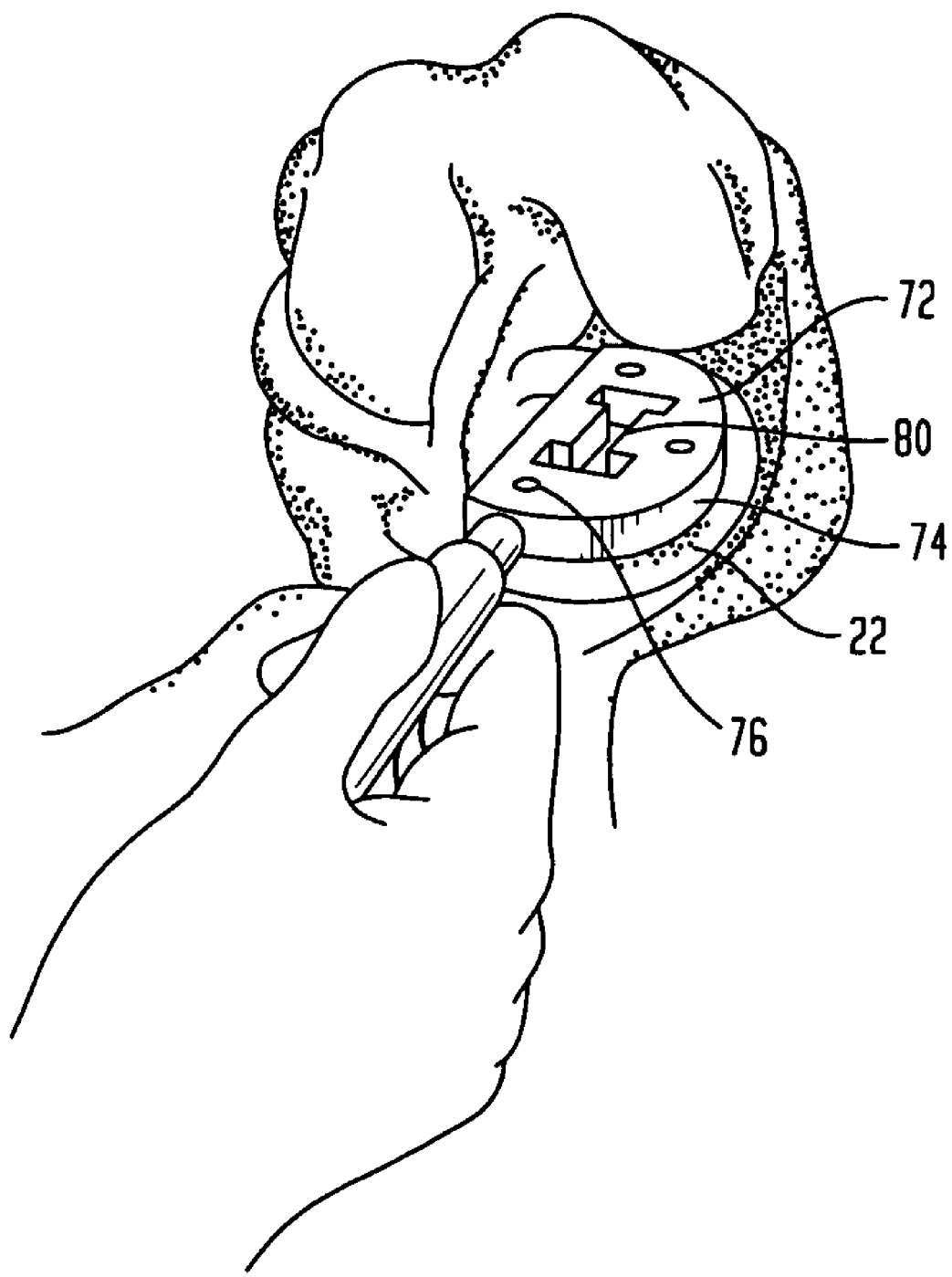
FIG. 7 shows an "I" beam template placed within the pocket milled in FIG. 6 on the resected tibial plateau.
Figure 8:
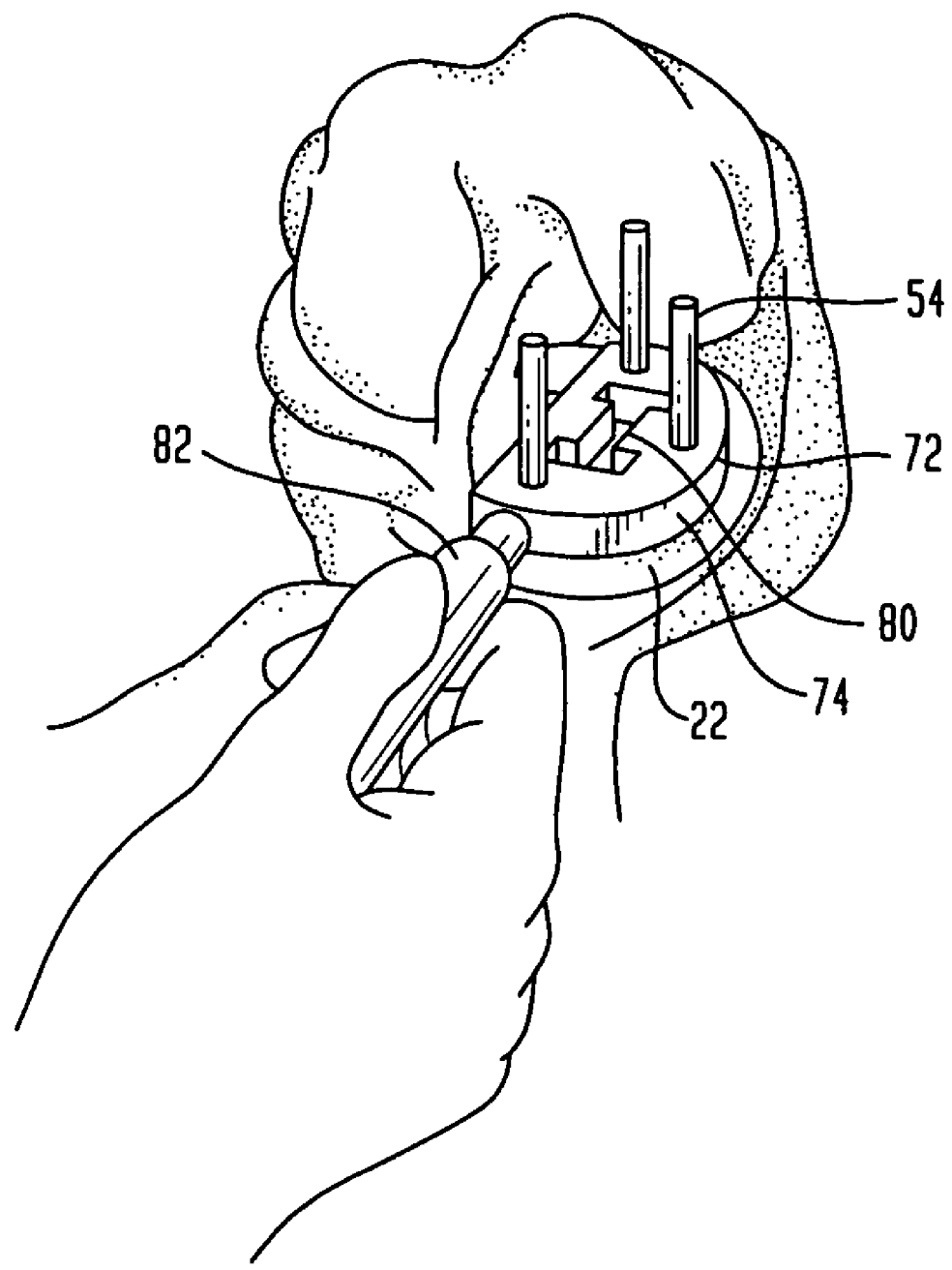
FIG. 8 shows the "I" beam template of FIG. 7 pinned in position.

Referring to FIGS. 7 and 8, there is shown a second template 72 having an outer surface 74 matching outer surface 44 of template 42. As shown in FIG. 8, template 72 includes a series of preferably three through holes 76 for receiving the same series of pins 54 as used for template 42. In the preferred embodiment, template 72 includes an "I"-shaped inner recess 80. While recess 80 is preferably "I"-shaped, it is conceivable that other shapes may be used which would the keel of receive an implant to be discussed below and prevent the translation and rotation thereof. Resection template 72 is located in a manner similar to that of resection template 42 and recess 80 is centrally located within the generally oval recess previously cut with template 42.

In the preferred embodiment, template 72 includes a handle 82 to facilitate its alignment on the tibial plateau. Pins 78 are placed through throughbores 76 and the original pin holes used with template 42 to maintain the resection template 72 in its aligned orientation. Alternately the pins used to hold down template 42 can be left in place and template 72 can be slid over the remaining pins.

Figure 9:
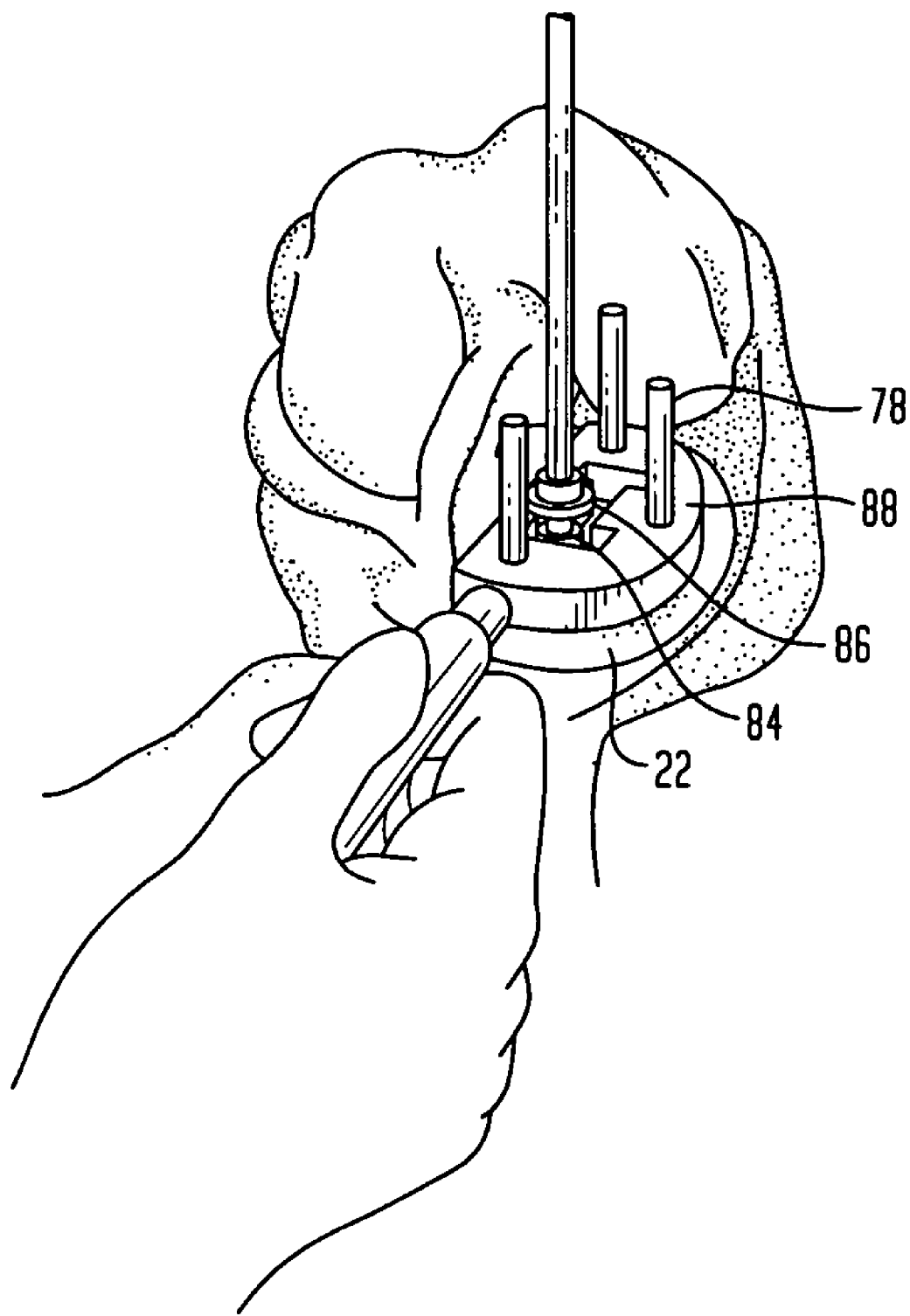
FIG. 9 shows a burr shaping the "I"-shaped pocket.

Referring to FIG. 9, a burr or end mill 84, which is similar or identical to end mill 60, is utilized to form an "I"-shaped recess within the oval recess already formed. Obviously, this recess has to be deeper into the tibial bone than the original oval shaped recess formed. Thus, burr 84 includes a stop plate 86 spaced at a greater distance from upper surface 88 of template 72 than stop 64 of burr or end mill 60. Generally, the thickness of template 42 and 72 will be identical, however, the dimensions between the bottom surface end mill or burr 84 and the guide surface 88 is dimensioned to produce an "I"-shaped recess of the desired depth. In the preferred embodiment, this depth is 0.240 inches and at least 0.2 inches below the recess surface initially formed in tibial plateau 24 with template 42.

Figure 10:
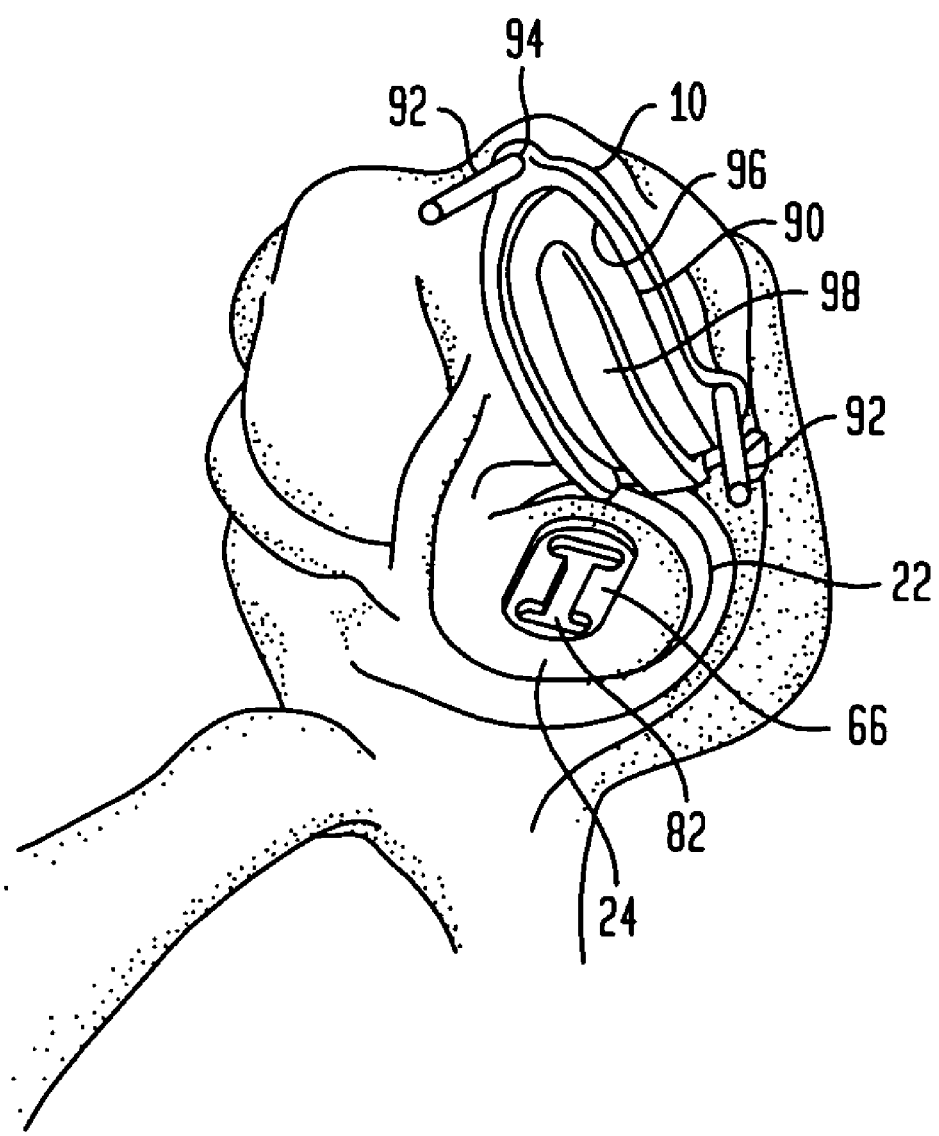
FIG. 10 shows the "I"-shaped pocket of FIG. 9 within the oval or "D"-shaped pocket formed in FIG. 6 along with a femoral burr template for forming a recess in the lateral femoral condyle.

Referring to FIG. 10 there is shown the two level recess formed in plateau 24. As discussed above, the recess has a first recessed area 66 and a more recessed area, in the shape of an "I", 82. As indicated above, the size of the resection templates 42 and 72 may change to match varying anatomy. In general, for each template 42 there will be a corresponding identically sized template 82. Consequently, if there are five templates 42 in a kit, there will be preferably five templates 82 in a kit. Thus, the size of the pockets or recesses 66, 82 will get larger as the template size increases. The use of the two depth recesses or pockets 66, 82 will be discussed below.

Referring again to FIG. 10, there is shown a femoral burr template 90 attached to lateral condyle 10 via pins 92. In the preferred embodiment, template 90 includes a pair of through bores 94 for receiving pins for attaching template 90 to the femoral condyle 10. Obviously, more pins 92 than two may be used. An end mill or burr similar to that discussed above with regard to elements 60, 84 is used to mill a recess within the inner surface 96 of template 90. If a thin wall of bone is left due to the center island, that remaining portion of bone is resected free-handed with the burr.

Figure 11:
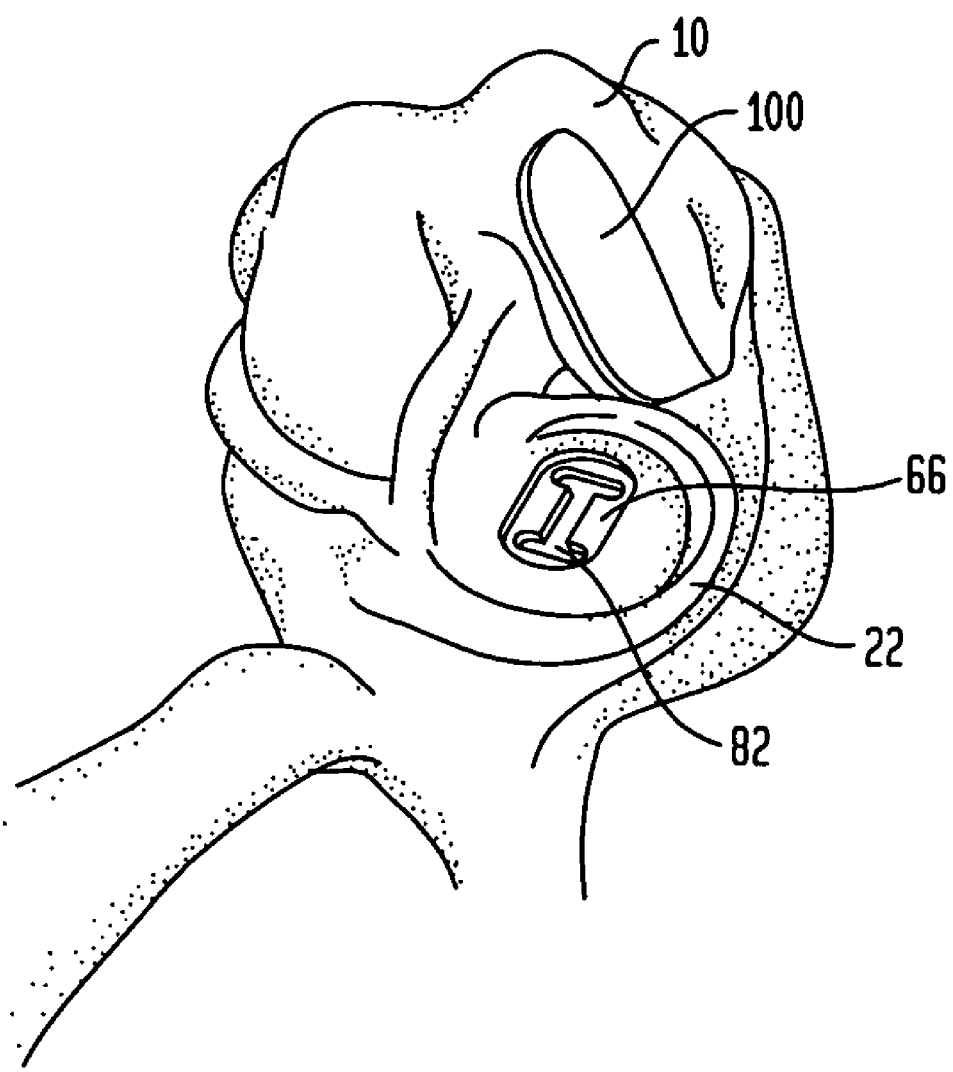
FIG. 11 shows the recess formed in FIG. 10.

As best seen in FIG. 11, a recess 100 is formed in the lateral condyle 10 of the femur.

Figure 12:
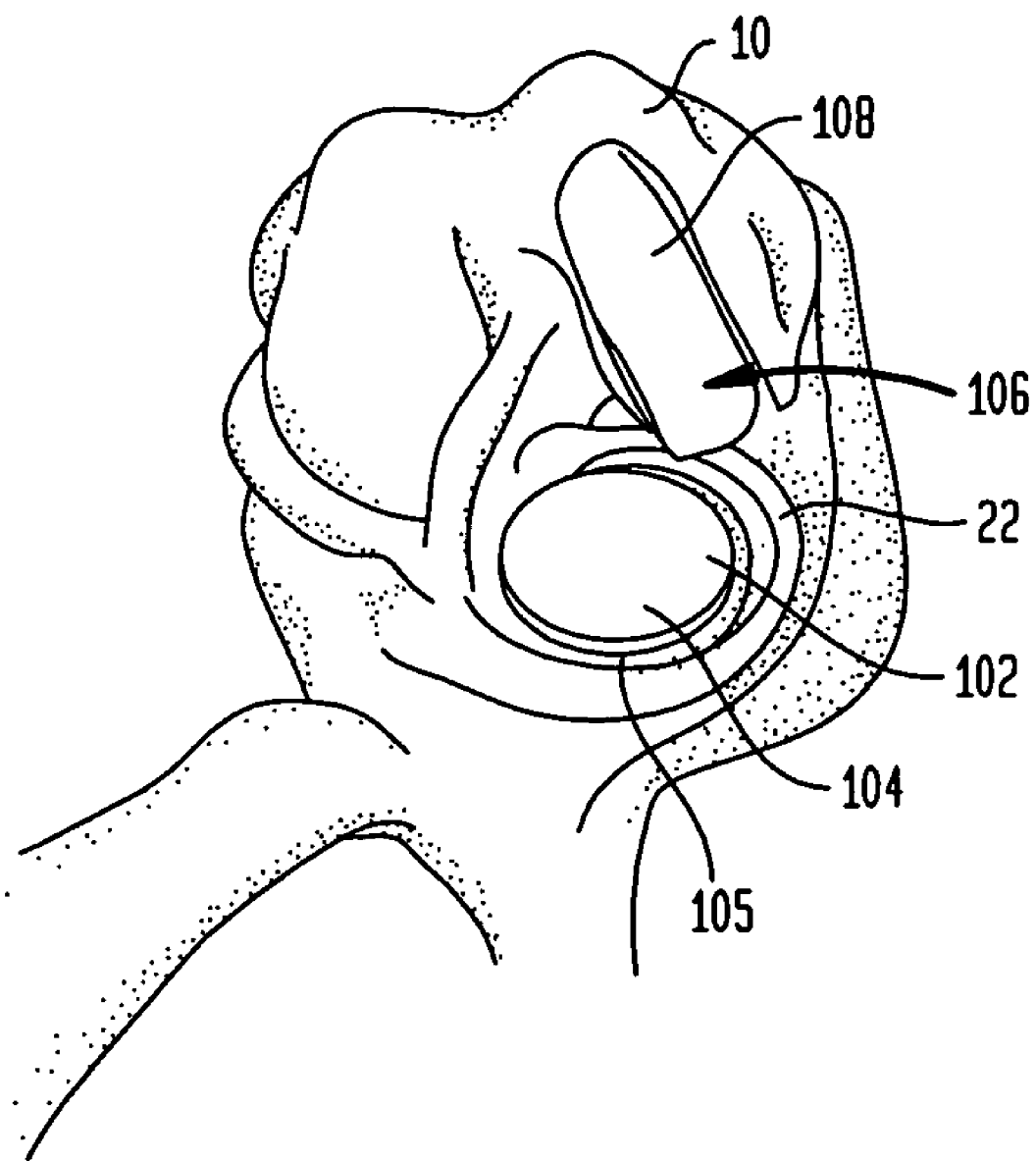
FIG. 12 shows both the femoral resurfacing implant on the femur and the tibial resurfacing implant attached to the tibial plateau.
Figure 13:
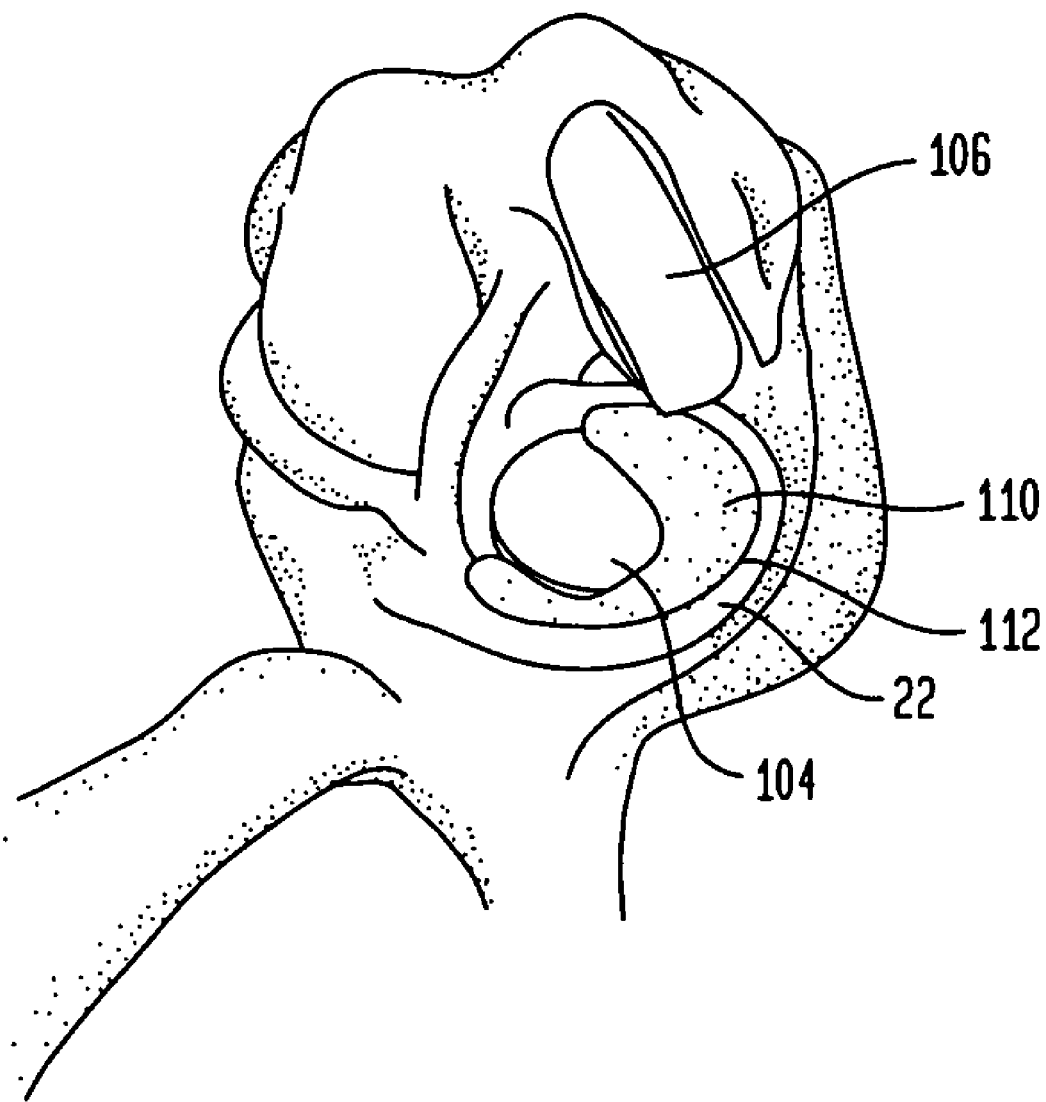
FIG. 13 shows the tibial resurfacing implant of FIG. 12 covered by a compliant meniscal implant which is attached to the remaining natural meniscal rim.
Figure 14:
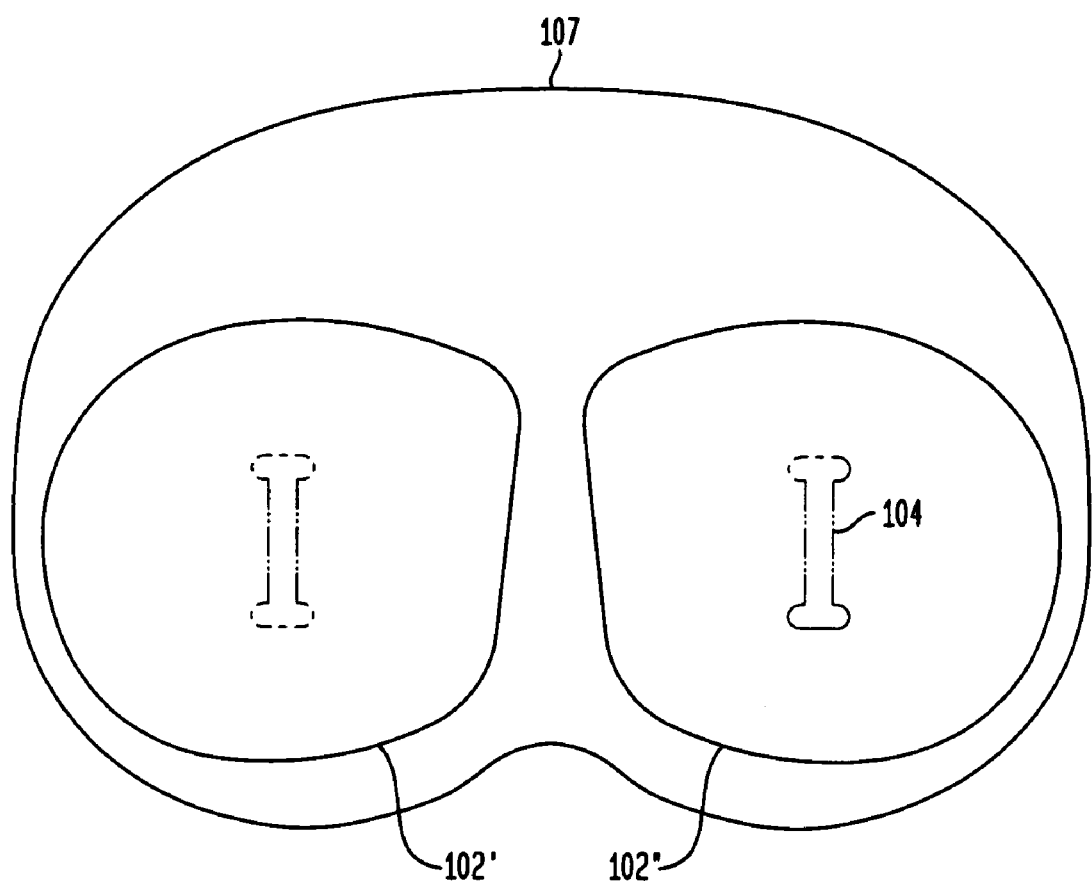
FIG. 14 is a bottom view of a medial and lateral tibial resurfacing implant including lateral implants of FIGS. 12 and 13.

Referring to FIGS. 12–14, there is shown the tibial and femoral resurfacing implants 102, 106 respectively. Tibial implant 102 includes an "I"-shaped keel 104 (shown in phantom in FIG. 12) which extends to the base of the "I"-shaped recess 82. Implant 102 has a periphery 105 which has a portion extending into the upper level, i.e., extending at a lesser distance from the base of the tibial resurfacing implant 104 and engaging with outer recess 66. Referring to FIG. 14, there is shown a bottom view of a preferred medial and lateral implant 102' and 102" each having a keel 104. The arcuate portion of the implants is placed adjacent remaining rim 22 of a tibial plateau 107. The tibial implant 102 is either press fit or cemented into recesses 66, 82. Femoral resurfacing implant 106 has an outer bearing surface 108 shaped to be congruent with the natural surface of the femoral condyle 10. Preferably, this component will be a cobalt chrome alloy implant having a thickness such that outer surface 108 is placed at or about the level of the natural femoral condyle 10 prior to resurfacing. Again, implant 108 may be either press fit or cemented into position. Alternately, the femoral resurfacing implant 106 may be made of a ceramic and cemented in position. In the preferred embodiment, tibial implant 104 is preferably made of polyethylene having a porous surface contacting the bone. Alternately, the tibial contact can be made of polyurethane, cobalt chrome, ceramic or a polyvinyl alcohol hydrogel.

Referring to FIG. 13, there is shown a meniscal implant 110 which is positioned proximally of the resurfacing implant 104. In the preferred embodiment, meniscal implant 110 is made of a polyvinyl alcohol hydrogel or a polyurethane but can be made of any biocompatible soft, compliant material that is able to withstand the loading in the knee joint and capable of the wear properties requires. Such a hydrogel meniscus is described in U.S. Publication No. 2002/0022884 published Feb. 21, 2002, the teachings of which are incorporated herein by reference. In the most preferred embodiment, the meniscus is made of a polyurethane which is molded to include an inner mesh or sutures. In the preferred embodiment, meniscal implant 110 is attached to the meniscal rim 22 via the sutures or mesh integrally molded into the hydrogel implant. Preferably, this is done around the entire circumference 112 of implant 110 so that it is maintained in position by the remaining natural meniscal rim 22. The mesh of the implant, for example that shown in U.S. Pat. No. 5,007,934, the teachings of which are incorporated herein by reference, may be coated or impregnated with bioactive factors, tissue cultures, BMPs or other resorbable polymers to encourage potential soft tissue ingrowth. This ingrowth would supplement or, in some cases, replace the suture attachment to meniscal rim 22.

While only the resurfacing of the lateral side of the tibial plateau and femur have been described, the process could as easily be used on the medial condyle 12 and medial tibial plateau.

The preferred surgical procedure utilizes a minimally invasive method which, when compared to standard techniques current used for resurfacing the knee joint of other body joints, uses a smaller incision. In this preferred method, the incision length is between 2 and 2 ½ times the patellar width. During forming the incision, everting or turning the patella over from its nature position should be avoided. Steps should also be taken to leave the quadriceps muscle 16 in its natural position by making sure it is not severed or twisted. Attachments to the peripheral tibial plateau such as horns 26, 28 and surrounding ligaments and musculature should be maintained through the meniscal rim 22. For example, the anterior cruciate ligament 14, if attached to the meniscal rim, should be maintained. Likewise the transverse ligament should be left attached to the meniscal horns. Initially, the posterior surface of the femur is prepared. This is done using femoral alignment guide 30 which has rod 32 extending externally of the incision, which rod points to the femoral head. The rod indicates implant flexion and implant rotation within the frontal and sagittal planes. Once properly aligned, a femoral sizing template 34 is used to measure and guide a posterior femoral cut. Obviously, there will be several different size templates corresponding to the several femoral implant sizes. The template may include guide 38 having saw blade slot 40 for preparing the posterior surface of the femur in a known manner.

Tibial sizing template 42 is then utilized to prepare the inner portion of the meniscus. Preferably, the meniscus will removed in an oval shape with the oval aligned via surface 50 with the two anatomic meniscal horns 26, 28. Obviously, again, there are various size templates 42 corresponding to different size tibias. Once aligned, the template 42 is pinned in position via pins 54 and burr 60 is used to mill pocket 66 into tibial plateau 24. A second "I" beam template 72 is placed over pins 54 after the initial template 42 is removed and a deeper recess is formed within the initial cavity. In other words, the "I"-shaped pocket 88 is deeper than the original "D"-shaped or oval pocket 66 to accommodate an "I"-shaped keel on the implant. Preferably, as the "D"-shaped pockets grow in size, the "I"-shaped keel receiving recess also grows. The "D"-shaped pocket 66 formed should encompass the maximum possible tibial plateau area within rim 22 with the "I"-shaped recess 82 in the center.

On the femoral side, a femoral burr template 90 is pinned in position via pins 92 and a recess of general uniform depth is formed, as by milling with a burr similar to burr 60 along with the condyle 10 of the distal femur. A femoral implant 106, preferably made of a cobalt chrome alloy such as Vitallium® alloy or a ceramic is implanted in the recess formed on the femoral condyle. Preferably, this implant has a thickness corresponding to the depth of the recess formed so that outer surface 108 of implant 106 is located at the correct anatomical position.

A tibial resurfacing implant 104 which may be circular or preferably have a general "D"-shape corresponding the various size template provided is implanted in recesses 66, 82. For each implant profile, several implant thicknesses are provided. The thickness is chosen such that the implant will be aligned in the varus/valgus direction. Once the implant thickness is determined, implant 104 will either be press fit or cemented into place. The tibial plateau implant bearing surface is preferably made of polyethylene and will have a porous metal surface against the bone. Alternatively, the tibial implant can be made of polyurethane, cobalt chrome, ceramics or a poly vinyl alcohol hydrogel. If the implant is made in the shape of a "D", the arcuate periphery of the "D" is located immediately inside the remaining rim 22 of the tibia.

Once the tibial plateau is resurfaced with implant 104, meniscal implant 10 is attached to the remaining meniscal rim 22 such by suturing. A sizing template is used to determine the required meniscal implant size in all three anatomical planes. The sizing template is similar to the D-shaped resection template with the arcuate portion sizing the meniscal implant. The meniscus, which is attached to remaining rim 22 of tibial plateau 24 preferably made of poly vinyl alcohol hydrogel or polyurethane but can be made of any biocompatible soft, compliant material that is able to withstand the functional loading and tribiological conditions. The implant is sutured into the remaining meniscal rim. The sutures can be made part of the implant such as by molding. See, for example, the implant of Kenny U.S. Pat. No. 4,344,193. The sutures may be made integral with a mesh that is also molded into the implant. The mesh can abut the meniscal rim and allow for the potential of soft tissue ingrowth. Bioactive factors such as tissue cultures, resorbables, bone morphogenic proteins can be added to the mesh to encourage the tissue ingrowth.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for resurfacing a joint capsule surface having cartilage and meniscal surfaces comprising:
   resecting a central portion of the joint cartilage and leaving a portion of the natural meniscal rim attached to the peripheral joint capsule, the portion of the natural meniscal rim having an inner surface;
   forming a cavity in a bone underlying said cartilage within said central portion;
   inserting a resurfacing implant into said cavity, said implant having a joint contact surface thereon; and
   suturing a prosthetic meniscal implant to said remaining meniscal rim said implant moveable on the joint contact surface of the resurfacing implant while sutured to said rim.

2. The method as set forth in claim 1 wherein said joint surface is a tibial surface having medial and lateral joint surfaces.

3. The method as set forth in claim 2 wherein at least one of said medial and lateral joint surfaces is resurfaced.

4. The method as set forth in claim 3 wherein said resection of said central portion of the joint surfaces leaves soft tissue joint attachment portions of the meniscus in tact.

5. The method as set forth in claim 1 wherein the cavity is stepped with a central portion of said cavity recessed into the underlying bone a greater depth than a surrounding recessed surface.

6. The method as set forth in claim 5 wherein said central portion of said cavity is the shape of an "I".

7. The method as set forth in claim 6 wherein said recess surrounding said central cavity is generally circular.

8. The method as set forth in claim 1 wherein the resurfacing implant is at least in part a polymeric implant.

9. The method as set forth in claim 8 wherein the resurfacing implant is made of a polymer selected from the group consisting of a polyethylene, polyvinyl alcohol hydrogel, and a polyurethane.

10. The method as set forth in claim 1 wherein the resurfacing implant is at least in part made of a cobalt chrome alloy.

11. The method as set forth in claim 10 wherein the cobalt chrome alloy meets the ASTM F75 standard.

12. The method as set forth in claim 1 wherein the resurfacing implant is at least in part made of a ceramic.

13. The method as set forth in claim 12 wherein the ceramic is selected from the group consisting of alumina, zirconia, zirconia toughened alumina, diamond, and diamond-like carbon.

14. The method as set forth in claim 1 wherein the prosthetic meniscal implant is made of a polymer selected from the group consisting of a polyvinyl alcohol hydrogel and a polyurethane.

15. The method as set forth in claim 14 further comprising molding a mesh fabric in said polymer.

16. The method as set forth in claim 8 wherein the polymer generates a fluid film bearing by imbibing aqueous fluid.

17. The method as set forth in claim 16 wherein the prosthetic meniscal implant is selected from the group consisting of a compliant polyvinyl alcohol hydrogel and a polyurethane.

18. The method as set forth in claim 17 further comprising suturing the meniscal implant to the meniscal rim.

19. The method as set forth in claim 17 further comprising attaching the resurfacing implant in said cavity by a method selected from the group consisting of cementing, suturing, press-fitting and a combination thereof.

20. The method as set forth in claim 1 wherein said cavity is formed at a depth so that said resurfacing implant has a bearing surface reproducing an original joint surface level.

21. A kit for resurfacing a tibial joint surface comprising:
   a plurality of joint resurfacing implants each having a metal base and a polymeric bearing surface;
   a plurality of polymeric meniscal implants capable of being sutured to a meniscal rim of the tibia and implants moveable on said polymeric bearing surface of said resurfacing implants;
   a plurality of templates for guiding the milling of bone underlying the joint surface; and
   at least one cutting element for engaging said template.

22. The kit as set forth in claim 21 wherein said templates have a D-shape.

23. The kit as set forth in claim 21 wherein said polymeric bearing surface is polyethylene and wherein said meniscal implant is made of polyurethane.

24. The kit as set forth in claim 21 wherein said cutting element is a burr having a drive shaft with a stop surface for engaging a surface on said templates.

* * * * *

UNITED STATES PATENT AND TRADEMARK OFFICE
CERTIFICATE OF CORRECTION

PATENT NO. : 6,994,730 B2  Page 1 of 1
APPLICATION NO. : 10/356263
DATED : February 7, 2006
INVENTOR(S) : Elliot Posner It is certified that error appears in the above-identified patent and that said Letters Patent is hereby corrected as shown below:

Column 12, line 51, "and" should read --and said--.

Signed and Sealed this

Second Day of October, 2007

JON W. DUDAS
*Director of the United States Patent and Trademark Office*